US00PP21725P2

(12) United States Plant Patent
Kraan

(10) Patent No.: US PP21,725 P2
(45) Date of Patent: Feb. 22, 2011

(54) ***WEIGELA* PLANT NAMED 'BOKRAFIVE'**
(50) Latin Name: *Weigela florida*
Varietal Denomination: Bokrafive

(75) Inventor: Kees Jan Kraan, Papenveer (NL)

(73) Assignee: Boot & Co. Boomkwekerijen BV, Booskoop (NL)

( * ) Notice: Subject to any disclaimer, the term of this patent is extended or adjusted under 35 U.S.C. 154(b) by 0 days.

(21) Appl. No.: 12/589,411

(22) Filed: Oct. 23, 2009

(51) Int. Cl.
*A01H 5/00* (2006.01)

(52) U.S. Cl. ..... Plt./226
(58) Field of Classification Search ..... Plt./226

See application file for complete search history.

*Primary Examiner*—June Hwu
*Assistant Examiner*—Louanne C Krawczewicz Myers
(74) *Attorney, Agent, or Firm*—Penny J. Aguirre

(57) ABSTRACT

A new cultivar of *Weigela florida,* 'Bokrafive', characterized by its glossy, blackish purple foliage and its very compact and nearly dwarf plant habit.

2 Drawing Sheets

Botanical classification: *Weigela florida.*
Variety denomination: 'Bokrafive'.

BACKGROUND OF THE INVENTION

The present invention relates to a new and distinct cultivar of *Weigela florida* and will be referred to hereafter by its cultivar name, 'Bokrafive'. 'Bokrafive' is a new cultivar of old fashion *Weigela,* a shrub grown for use as an ornamental landscape plant.

The new cultivar of *Weigela* is a selection from an ongoing breeding program conducted by the Inventor in Boskoop, The Netherlands with the objective of creating new cultivars of *Weigela* with compact plant habits and attractive foliage coloration.

The new variety of *Weigela*, 'Bokrafive', designated as accession no. 00090-05 was selected from seedlings derived from a cross made in summer of 2000 between unnamed proprietary seedlings of *Weigela florida.* The female parent, designated as accession no. 93115, derived from open pollination of the cultivar 'Evita' (not patented). The male parent of 'Bokrafive' is unknown. After 6 years of observation, 'Bokrafive' was selected as a single unique plant in summer of 2007.

Asexual reproduction of the new cultivar was first accomplished by the Inventor using softwood stem cuttings in summer of 2007 in Boskoop, The Netherlands. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for eight years in Boskoop, The Netherlands. These attributes in combination distinguish 'Bokrafive' as a unique cultivar of *Weigela.*

1. 'Bokrafive' exhibits a very compact and nearly dwarf plant habit.
2. 'Bokrafive' exhibits glossy, blackish purple foliage.

The female parent, no. 93115, differs from 'Bokrafive' in having a much less compact plant habit, in having glossy dark green foliage and in being more floriferous. 'Bokrafive' can be most closely compared to the cultivars 'Victoria' and 'Minuet' (both unpatented). 'Victoria' differs from 'Bokrafive' in having a taller and much less compact plant habit and in having foliage that is dull and brownish-green in color. 'Minuet' differs from 'Bokrafive' in having a less compact and more spreading plant habit, in having foliage that is brownish-green in color and in being more floriferous.

BRIEF DESCRIPTION OF THE DRAWING

The accompanying colored photographs were taken in May and illustrate the overall appearance and distinct characteristics of 8 year-old plants the new *Weigela* as grown in a trial plot in Boskoop, The Netherlands.

The photograph in FIG. 1 provides an overall view of the growth habit and blooming habit of 'Bokrafive'.

Figure 1:
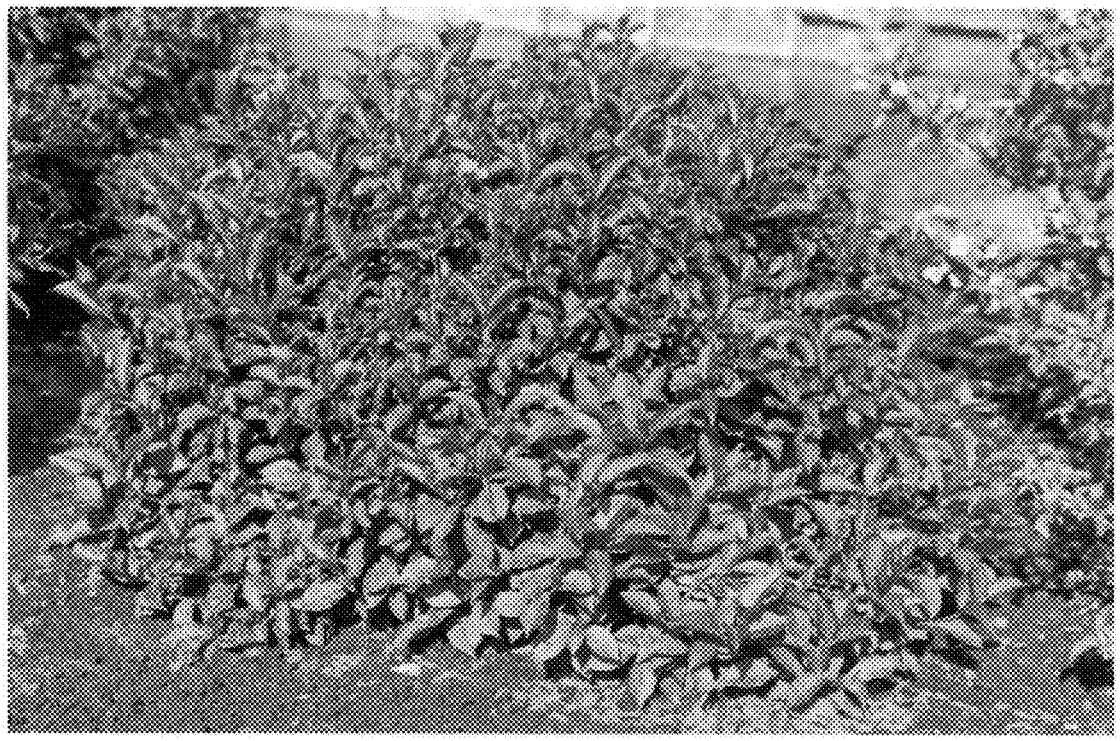
Figure 2:
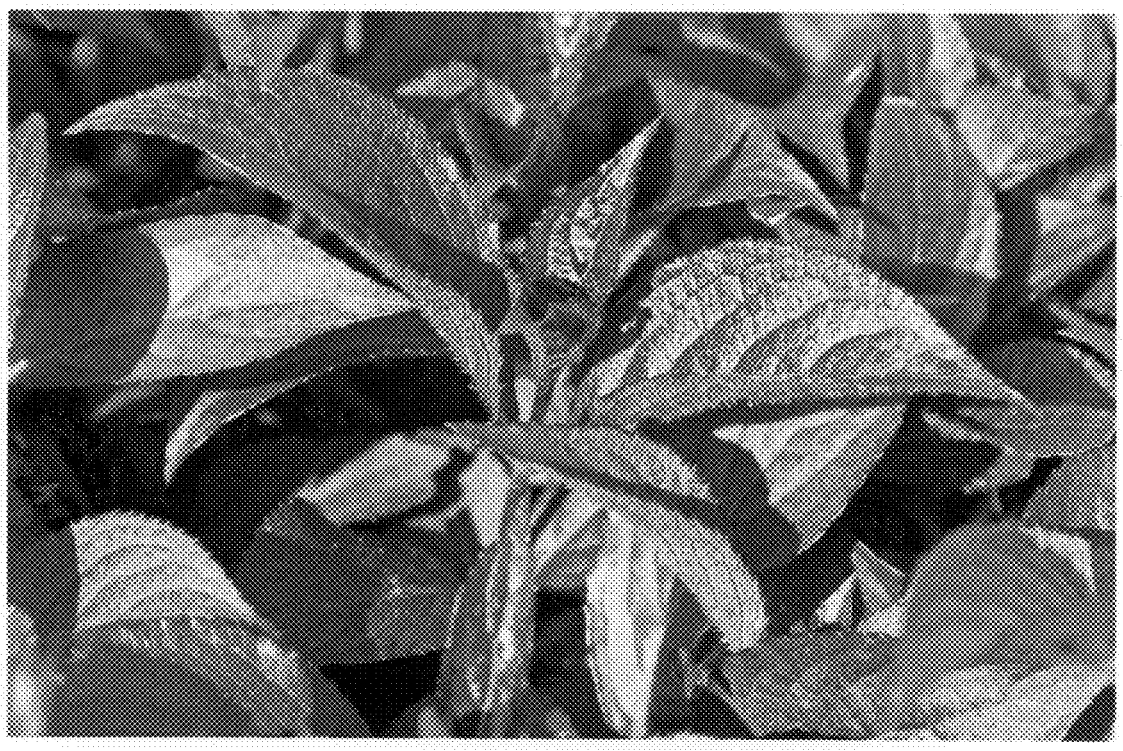

The photograph in FIG. 2 provides a close-up view of the foliage of 'Bokrafive'.

Figure 3:
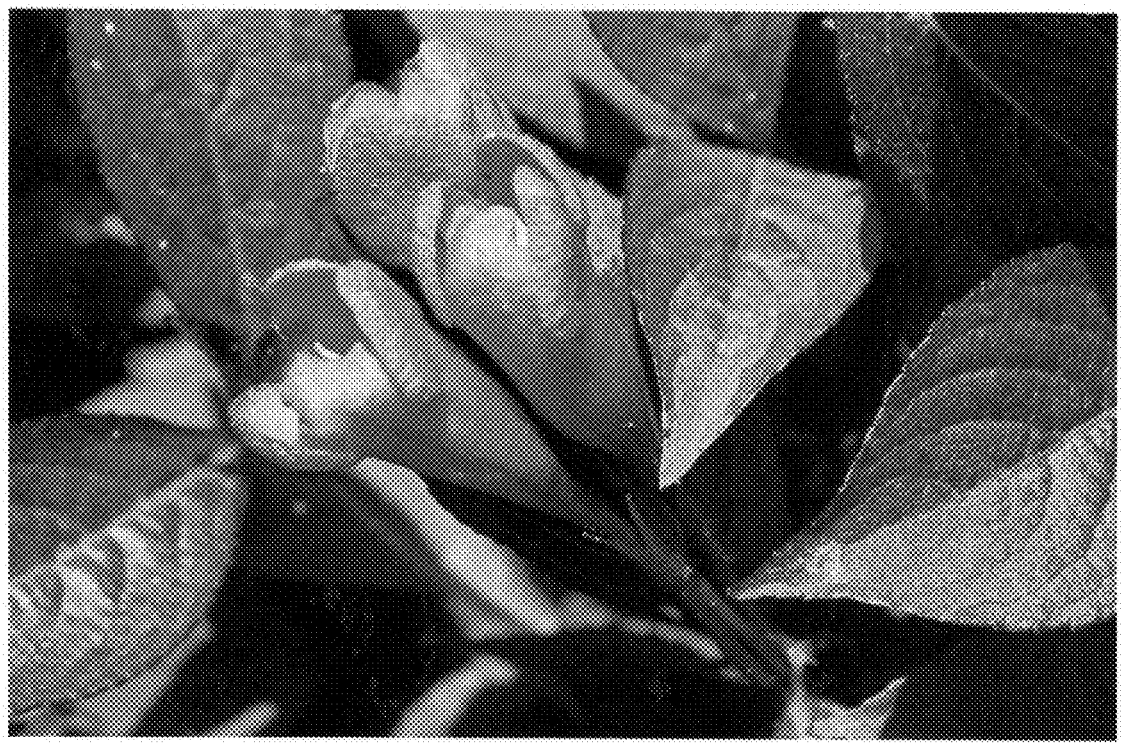

The photograph in FIG. 3 provides a close-up view of the flowers of 'Bokrafive'. The colors in the photograph may differ slightly from the color values cited in the detailed botanical description, which accurately describe the colors of the new *Weigela.*

DETAILED BOTANICAL DESCRIPTION

The following is a detailed description of 8 year-old plants of the new cultivar as grown outdoors in full sun in a trial plot in Boskoop, The Netherlands. Plants were grown under average day temperatures of 15° C. to 28° C. and average night temperature of 7° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for about 3 weeks in May in Boskoop, The Netherlands.

*Plant type.*—Deciduous shrub.

*Plant habit.*—Very compact, broadly upright, freely branched, nearly dwarf stature.

*Plant size.*—Reaches about 50 cm in height and 82 cm in width.

*Hardiness.*—At least in U.S.D.A. Zones 5 to 9.

*Environmental stress.*—Highly tolerant to wind and rain.

*Diseases and pests.*—No susceptibility or resistance to diseases or pests has been observed, similar to other *Weigela* known to the Inventor.

*Root description.*—Fibrous, moderately dense.

Growth and propagation:

*Propagation.*—Softwood stem cuttings.

*Root initiation.*—An average of 30 days at soil temperatures of 20° C.

*Root development.*—An average of 26 weeks at air temperatures of 18° C. to finish a young plant.

*Growth rate.*—Moderate, about 4 cm per month in spring.

Stem description:

*Shape.*—Slightly quadrangular with older branches rounded.

*Stem color.*—New growth; 183A and 183B tinged at nodes with145A, mature wood; 199B and 199C.

*Stem size.*—An average of 22.3 cm in length and 2 mm in diameter.

*Stem surface.*—New growth; moderately glossy with more terminal portion of stems pubescent with hairs about 0.5 mm in length and 155B in color, mature wood is dull and glabrous.

*Stem aspect.*—Upright to outward at an average angle of 45°.

*Branching.*—Basal branching, an average of 168 lateral branches.

Foliage description:

*Leaf shape.*—Elliptic.

*Leaf division.*—Simple.

*Leaf base.*—Short attenuate.

*Leaf apex.*—Acuminate.

*Leaf fragrance.*—None.

*Leaf venation.*—Pinnate, color upper surface 144B, color lower surface 145A and tinged with 183B and 183C.

*Leaf margins.*—Finely serrate, pubescent with hairs about 0.75 mm in length and 158B and 158C in color.

*Leaf arrangement.*—Opposite.

*Leaf attachment.*—Petiolate.

*Leaf surface.*—Upper surface; glossy with main vein moderately covered with hairs about 0.75 mm in length and 158B and 158C in color, lower surface; glossy and moderately covered with hairs about 0.5 mm in length and 158C and 158D in color.

*Leaf internode length.*—An average of 2.6 cm.

*Leaf size.*—An average of 4.3 cm in length and 2.2 cm in width.

*Leaf quantity.*—An average of 16 per stem.

*Leaf color.*—Newly expanded leaves; upper surface 200A and lower surface 200A and 200B, mature leaves; upper surface 147A and tinged with N200B and lower surface N200B.

*Petioles.*—About 5 mm in length and 1.5 mm in width, color 145A and tinged with 183B and 183C.

*Stipules.*—None.

Inflorescence description:

*Inflorescence type.*—Solitary, in pairs, or in small clusters at terminus and leaf axils.

*Inflorescence size.*—From of 1.4 cm in diameter and 3.6 cm in depth when a solitary flower and up to 3.2 cm in depth and 10 cm in diameter when in clusters.

*Flower buds.*—Narrowly obovate in shape, an average of 2.8 cm in depth and 8 mm in diameter, 61A in color with basal portion 59A.

*Flower fragrance.*—None.

*Lastingness of flowers.*—About 12 days with about 90% of flowers in bloom at one stage, self-cleaning.

*Flower aspect.*—Outward to upright.

*Flower quantity.*—An average of 20 per stem, an average of 3,000 per plant 8 years in age.

*Flower type.*—Tubular.

*Flower size.*—Average of 1.4 cm in diameter and 3.6 cm in depth.

*Peduncles.*—Average of 1.5 cm in length and 1 mm in diameter, color is a color between 175A and N199B, glabrous surface, oval in shape.

*Pedicels.*—None, sessile to peduncle.

*Calyx.*—Rotate in shape, an average of 9 mm in depth and 6 mm in width.

*Sepals.*—5, linear in shape, narrowly acute apex, narrowly cuneate base, entire margin, an average of 9 mm in length and 1 mm in width, color on upper surface when opening and mature is 148A and 148B with upper half heavily tinged with N186C, color on lower surface when opening and mature is a color between N186C and 200A, surface is slightly glossy on both surfaces.

*Petals.*—5, lower 75% fused into tube, spathulate in shape, margin entire on free portion, apex obtuse, an average of 3.6 cm in length with free portion an average of 1 cm in width, outer and inner surface is smooth and slightly glossy, color of inner surface when opening and mature; 70B blending with 68A with tube portion 64B, color of outer surface when opening and mature; 61A with tube portion 59B, color of both surfaces fade to 70B.

Reproductive organs:

*Gynoecium.*—1 pistil, about 3.5 cm in length, style is an average of 3.3 cm in length, and 59C in color, stigma is deformed into anther-like structure, ovary is a color between N186C and 200A.

*Androcoecium.*—5 stamens, filaments are 59C in color and an average of 1.3 cm in length, anthers are 160B to 160C in color, an average of 3 mm in length, basifixed and narrowly oblong in shape, pollen is low in quantity and 158D in color.

*Fruit and seed.*—No fruit or seed production has been observed to date.

It is claimed:

1. A new and distinct cultivar of *Weigela* plant named 'Bokrafive' as herein illustrated and described.

* * * * *